United States Patent
Abel et al.

(10) Patent No.: US 12,326,971 B1
(45) Date of Patent: Jun. 10, 2025

(54) SYSTEM AND METHOD FOR FACILITATING ADAPTIVE RECENTERING IN VIRTUAL REALITY ENVIRONMENTS

(71) Applicant: Bansen Labs, Pittsburgh, PA (US)

(72) Inventors: Ray Abel, Pittsburgh, PA (US); Qiqing Zhang, Pittsburgh, PA (US)

(73) Assignee: Bansen Labs, LLC, Pittsburgh, PA (US)

( * ) Notice: Subject to any disclaimer, the term of this patent is extended or adjusted under 35 U.S.C. 154(b) by 0 days.

(21) Appl. No.: 18/905,868

(22) Filed: Oct. 3, 2024

(51) Int. Cl.
| | |
|---|---|
| *G06F 3/01* | (2006.01) |
| *G06F 3/04815* | (2022.01) |
| *G06F 3/04845* | (2022.01) |
| *G06F 3/0485* | (2022.01) |

(52) U.S. Cl.
CPC .............. *G06F 3/012* (2013.01); *G06F 3/013* (2013.01); *A61B 2505/00* (2013.01); *A61B 2505/09* (2013.01); *A63B 2230/605* (2013.01); *G06F 3/011* (2013.01); *G06F 3/04815* (2013.01); *G06F 3/04845* (2013.01); *G06F 3/0485* (2013.01)

(58) Field of Classification Search
CPC .............. G06F 3/0485; G06F 3/04845; G06F 3/04815; G06F 3/013; G06F 3/012; G06F 3/011; A63B 2230/605; A61B 2505/09; A61B 2505/00
See application file for complete search history.

(56) References Cited

U.S. PATENT DOCUMENTS

| | | |
|---|---|---|
| 7,094,153 B2 | 8/2006 | Kunieda et al. |
| 7,883,415 B2 | 2/2011 | Larsen et al. |
| 8,408,706 B2 | 4/2013 | Yahav |
| 8,576,276 B2 | 11/2013 | Bar-Zeev et al. |
| 8,797,321 B1 | 8/2014 | Bertolami et al. |
| 8,810,600 B2 | 8/2014 | Bohn et al. |
| 8,878,846 B1 | 11/2014 | Francis, Jr. et al. |
| 8,928,558 B2 | 1/2015 | Lewis et al. |
| 8,933,912 B2 | 1/2015 | Ambrus et al. |
| 8,941,559 B2 | 1/2015 | Bar-Zeev et al. |
| 8,964,298 B2 | 2/2015 | Haddick et al. |
| 9,050,538 B2 | 6/2015 | Sugiyama et al. |
| 9,152,402 B2 | 10/2015 | Scheidel et al. |
| 9,159,165 B2 | 10/2015 | Stafford et al. |
| 9,207,455 B2 | 12/2015 | Bickerstaff et al. |
| 9,285,872 B1 | 3/2016 | Raffle et al. |
| 9,454,849 B2 | 9/2016 | Mount et al. |
| 9,524,580 B2 | 12/2016 | Katz et al. |
| 9,530,227 B2 | 12/2016 | Nevin, III |
| 9,595,113 B2 | 3/2017 | Osa et al. |

(Continued)

FOREIGN PATENT DOCUMENTS

WO 2022013894 A1 1/2022

*Primary Examiner* — Mihir K Rayan
(74) *Attorney, Agent, or Firm* — White and Williams LLP

(57) ABSTRACT

The present invention pertains to a system and method for facilitating adaptive recentering in virtual reality ("VR") environments capable of autonomously monitoring a user's viewpoint orientation within a VR environment using integrate sensors to detect deviations exceeding a predetermined threshold angle from a central reference point. The system employs an algorithm to evaluate the duration and extent of the user's viewpoint deviation, enabling detection of potential recentering needs without requiring direct physical input.

20 Claims, 9 Drawing Sheets

(56) References Cited

U.S. PATENT DOCUMENTS

| | | |
|---|---|---|
| 9,659,403 B1 | 5/2017 | Horowitz |
| 9,659,413 B2 | 5/2017 | Grossinger et al. |
| 9,667,860 B2 | 5/2017 | Hakim et al. |
| 9,681,804 B2 | 6/2017 | Spitzer |
| 9,690,374 B2 | 6/2017 | Clement et al. |
| 9,766,712 B2 | 9/2017 | Schpok |
| 9,767,613 B1 | 9/2017 | Bedikian et al. |
| 9,823,744 B2 | 11/2017 | Publicover et al. |
| 9,858,703 B2 | 1/2018 | Kaminitz et al. |
| 9,877,016 B2 | 1/2018 | Esteban et al. |
| 9,911,032 B2 | 3/2018 | Shotton et al. |
| 9,990,774 B2 | 6/2018 | Mao |
| 9,996,797 B1 | 6/2018 | Holz et al. |
| 10,025,060 B2 | 7/2018 | Lanman et al. |
| 10,038,887 B2 | 7/2018 | Gallup et al. |
| 10,043,281 B2 | 8/2018 | Mallinson et al. |
| 10,078,218 B2 | 9/2018 | Katz et al. |
| 10,078,367 B2 | 9/2018 | Michail et al. |
| 10,095,036 B2 | 10/2018 | Carollo et al. |
| 10,121,299 B2 | 11/2018 | Kusens et al. |
| 10,126,822 B2 | 11/2018 | Cohen et al. |
| 10,127,632 B1 | 11/2018 | Burke et al. |
| 10,180,720 B2 | 1/2019 | Higgins et al. |
| 10,198,032 B2 | 2/2019 | Thomas |
| 10,198,874 B2 | 2/2019 | Dearman et al. |
| 10,203,762 B2 | 2/2019 | Bradski et al. |
| 10,229,312 B2 | 3/2019 | Barnett et al. |
| 10,241,569 B2 | 3/2019 | Lanman et al. |
| 10,275,025 B2 | 4/2019 | Black et al. |
| 10,306,202 B2 | 5/2019 | Raghoebardajal et al. |
| 10,338,687 B2 | 7/2019 | Glazier et al. |
| 10,380,228 B2 | 8/2019 | Lee |
| 10,416,837 B2 | 9/2019 | Reif |
| 10,423,226 B2 | 9/2019 | Chen et al. |
| 10,429,647 B2 | 10/2019 | Gollier et al. |
| 10,437,347 B2 | 10/2019 | Holz et al. |
| 10,445,925 B2 | 10/2019 | Tokubo |
| 10,453,175 B2 | 10/2019 | Mierle et al. |
| 10,475,249 B2 | 11/2019 | Holz et al. |
| 10,496,156 B2 | 12/2019 | Tilton et al. |
| 10,657,701 B2 | 5/2020 | Osman et al. |
| 10,665,205 B2 | 5/2020 | Weaver et al. |
| 10,670,928 B2 | 6/2020 | Shi et al. |
| 10,733,431 B2 | 8/2020 | Zhang et al. |
| 10,733,781 B2 | 8/2020 | Shenton et al. |
| 10,796,185 B2 | 10/2020 | Collet Romea et al. |
| 10,878,631 B2 | 12/2020 | Dange |
| 10,890,941 B2 | 1/2021 | Raffle et al. |
| 10,908,682 B2 | 2/2021 | Goossens |
| 10,909,747 B2 | 2/2021 | Yu et al. |
| 10,916,065 B2 | 2/2021 | Furtwangler et al. |
| 10,921,878 B2 | 2/2021 | Noris et al. |
| 11,024,086 B2 | 6/2021 | Tate-Gans et al. |
| 11,058,950 B2 | 7/2021 | Azmandian et al. |
| 11,080,937 B2 | 8/2021 | Holz |
| 11,099,652 B2 | 8/2021 | Osotio et al. |
| 11,151,699 B2 | 10/2021 | Rodriguez et al. |
| 11,181,990 B2 | 11/2021 | Marks et al. |
| 11,237,625 B2 | 2/2022 | Johnston et al. |
| 11,269,481 B2 | 3/2022 | Holz |
| 11,536,973 B2 | 12/2022 | Miller et al. |
| 11,668,930 B1 | 6/2023 | Pennell et al. |
| 11,741,649 B2 | 8/2023 | Pollard et al. |
| 11,966,059 B2 | 4/2024 | Welch et al. |
| 12,007,573 B2 | 6/2024 | Yeoh et al. |
| 2014/0361977 A1 | 12/2014 | Stafford et al. |
| 2016/0054837 A1 | 2/2016 | Stafford |
| 2017/0078447 A1 | 3/2017 | Hancock et al. |
| 2018/0024363 A1 | 1/2018 | Wong et al. |
| 2018/0095635 A1 | 4/2018 | Valdivia et al. |
| 2018/0095637 A1 | 4/2018 | Valdivia et al. |
| 2018/0113508 A1 | 4/2018 | Berkner-Cieslicki et al. |
| 2019/0011982 A1 | 1/2019 | Wheeler et al. |
| 2019/0033989 A1 | 1/2019 | Wang et al. |
| 2019/0043259 A1 | 2/2019 | Wang et al. |
| 2020/0097603 A1 | 3/2020 | Vangala et al. |
| 2020/0401422 A1 | 12/2020 | Liu et al. |
| 2021/0117214 A1 | 4/2021 | Presant et al. |
| 2023/0214005 A1 | 7/2023 | Ohashi |
| 2023/0394621 A1 | 12/2023 | Nourai et al. |
| 2023/0414899 A1 | 12/2023 | Mallinson |
| 2024/0031547 A1 | 1/2024 | Holz et al. |
| 2024/0061636 A1 | 2/2024 | Yu |
| 2024/0192772 A1* | 6/2024 | Lutter ............... G06F 3/011 |

* cited by examiner

SYSTEM AND METHOD FOR FACILITATING ADAPTIVE RECENTERING IN VIRTUAL REALITY ENVIRONMENTS

BACKGROUND OF THE INVENTION

The present invention is directed to a system and method for facilitating adaptive recentering in virtual reality ("VR") environments. The use of VR has recently expanded into several different fields including gaming, entertainment, business, scientific research, education, and more. VR offers immersive advantages including realistic simulations, risk-free practice, and experiential training. Overall, VR provides a unique opportunity to immerse a user in a virtual environment that could otherwise be challenging, unsafe, or impossible to achieve in the real world. However, the advantages of VR come with several challenges including limited accessibility for users with mental or physical disabilities or impairments. The present invention provides a system and method for facilitating adaptive recentering in virtual reality ("VR") environments in order to increase the accessibility of VR and provide a more seamless experience overall for any user.

In immersive VR gaming experiences, the adaptive recentering system can enhance accessibility for players with limited mobility or physical disabilities. As players engage in virtual battles or explore vast virtual worlds, the system can automatically prompt recentering when their viewpoint deviates significantly, allowing them to seamlessly adjust their perspective without disrupting the gameplay.

For VR cinema or theater experiences, the recentering system can ensure that viewers with disabilities can comfortably enjoy the virtual performance by automatically adjusting their viewpoint to the optimal vantage point without requiring manual inputs or assistance. In VR-based educational simulations or virtual classrooms, the adaptive recentering feature can assist students with disabilities in maintaining a focused and optimal viewpoint during lectures, demonstrations, or interactive learning experiences, enhancing their engagement and comprehension.

Architects and designers can leverage the adaptive recentering system in VR walkthroughs of proposed building designs or virtual models. As they navigate the virtual spaces, the system can automatically recenter their viewpoint, enabling them to inspect intricate details or visualize the design from different perspectives without manually adjusting their position. In virtual reality tourism experiences, the recentering system can enhance the immersive experience for users with disabilities by automatically adjusting their viewpoint to capture the most captivating angles of famous landmarks or natural wonders without needing physical inputs that could be challenging or impossible for some users.

Furthermore, adaptive recentering technology can by integrated into VR-based therapy or rehabilitation programs for individuals with physical or cognitive impairments. As patients engage in virtual exercises or simulations, the system can dynamically adjust their viewpoint, ensuring they maintain the optimal perspective for effective therapy sessions without strain or discomfort.

SUMMARY OF THE INVENTION

The present invention pertains to a system and method for facilitating adaptive recentering in virtual reality (VR) environments. The system autonomously monitors the user's viewpoint orientation within a VR environment using integrate sensors, such as gyroscopes and accelerometers, to detect deviations exceeding a predetermined threshold angle from a central reference point. Utilizing an innovative approach, the system employs an algorithm to evaluate the duration and extent of the user's viewpoint deviation, enabling detection of potential recentering needs without requiring direct physical input. Upon detecting a significant deviation indicative of a recentering requirement, the system dynamically generates a recentering prompt within the VR environment, seamlessly integrating the prompt into the ongoing user interaction. This prompt facilitates an intuitive recentering process, allowing users to easily adjust their viewpoint with minimal effort and without the need for additional hardware inputs, such as adaptive input devices.

Moreover, the system can discern intentional from unintentional deviations, dismissing the recentering prompt when the user's viewpoint returns within the acceptable range, ensuring a continuous and uninterrupted VR experience. The disclosed methods and systems significantly enhance accessibility for users with disabilities, leveraging minimal input for maximum navigational control within VR environments. This adaptive recentering approach simplifies the user interface and promotes a more inclusive and accessible VR experience across various applications and user demographics.

The present invention's recentering system employs a multi-faceted approach, incorporating hardware and software components to deliver an innovative solution to user recentering VR environments. The core elements of the system include widespread sensor compatibility, user interaction detection, recentering prompt generation, and multi-channel user feedback.

The system leverages standard sensors in most VR headsets, such as gyroscopes, accelerometers, and magnetometers. This ensures that the adaptive recentering functionality can be implemented across various VR devices without the need for additional hardware modifications. Gyroscopes are used to measure the angular velocity of the user's head movements. They provide precise data on the rotational movement along the X, Y, and Z axes. This allows the system to detect the direction and speed of head turns, which is crucial for identifying deviations from the central reference point. Accelerometers measure the linear acceleration of the user's head. They help in determining the tilt and inclination of the head by detecting changes in velocity. This is essential for understanding the overall head movement and orientation within the VR environment. Magnetometers are used to measure the orientation of the user's head relative to the earth's magnetic field. They help provide an absolute reference point for orientation, which complements the data from gyroscopes and accelerometers. This ensures accurate tracking of the user's head position and movement.

A sophisticated adaptive algorithm processes and analyzes user data from integrated sensors in real-time to detect deviations from a central reference point. The algorithm evaluates the magnitude and duration of these deviations to determine when recentering is necessary. The adaptive recentering process involves several key steps, beginning with deviation detection. The algorithm continuously monitors the user's head movement using integrated hardware sensors, such as gyroscopes and accelerometers, to measure the current viewpoint orientation. When the deviation angle exceeds a predefined threshold, a timer is initiated. The next step is prompt generation. If a deviation persists beyond the specified waiting time, a recentering prompt is generated and displayed to the user within the VR environment. Following the prompt generation, the system tracks how the user responds to the recentering prompt. If the user presses a button to recenter, this indicates that the prompt was necessary, and the system records this as a "successful response." If the user ignores the prompt and manually adjusts their viewpoint to return within the acceptable range, this is recorded as an "automatic recovery." Following this, the algorithm dynamically adjusts the detection threshold based on user interaction data. Initially, the threshold is adjusted based on all available historical data. As more data is collected, the algorithm places greater emphasis on recent interactions. If the user frequently achieves automatic recovery without requiring a prompt, the threshold is increased to accommodate the user's ability to control the deviation. On the other hand, if the user consistently responds to prompts by interacting with the recenter prompt, indicating the prompt is needed, the threshold is decreased to prompt recentering sooner.

The system then continuously monitors the user's viewpoint and adjusts the threshold in real-time, ensuring that the adaptive recentering remains aligned with the user's specific needs and behaviors. The system also allows users to customize the sensitivity of the recentering prompts, providing flexibility to tailor the system's responsiveness according to their specific needs and preferences. Key customization options include angular threshold adjustment, prompt frequency, sensitivity of response, and response time. Specifically, users can modify the initial angular threshold, which determines how much deviation from the central reference point is allowed before a recentering prompt is triggered. This allows users to set a threshold that best suits their comfort level and movement patterns within the VR environment. Users can also adjust how often the system checks deviations and generates recentering prompts. By setting the prompt frequency, users can control how quickly the system responds to significant deviations, ensuring the prompts are timely without being overly intrusive. The system's responsiveness can be fine-tuned based on user interaction data. Users can customize how the system dynamically adjusts the threshold based on their behavior. For instance, users can set how aggressively the system should increase or decrease the threshold based on their manual adjustments or button presses. Users can also set the waiting time before a recentering prompt is displayed after detecting a deviation. This allows users to balance immediate feedback and giving themselves a chance to self-correct without interruption. By incorporating these adaptive mechanisms and customization options, the system remains responsive to the user's behavior, providing prompts only when necessary and allowing for a more natural and seamless VR experience. This flexibility enhances the overall user experience, making the VR environment more accessible and comfortable for a diverse range of users.

Upon identifying a significant deviation, the system generates a recentering prompt within the VR environment. This prompt seamlessly integrates into the user's current interaction, minimizing disruption and facilitating an intuitive recentering process. The detailed steps involved include state recording, wherein the system automatically records the player's current progress state before displaying the recenter prompt. This current progress state may, for example, include a highlighted menu option in the player's view. By recording this state, the system ensures that the user's context is preserved for a smooth transition back to their original task after recentering. The recentering prompt is then displayed within the VR environment. To minimize disruption, the prompt is designed to be easily accessible and intuitive. The system automatically sets the highlighted option to the recenter option, enabling users to quickly and effortlessly respond to the prompt. Whether the user responds to the recentering prompt by pressing a button or manually adjusts their view to return within the acceptable range, the system ensures a seamless transition by automatically restoring the previously recorded states after recentering the user's view. For example, this may include resetting a highlighted option to its original state, allowing users to continue their menu interaction without interruption. By implementing these steps, the system ensures that the recentering process is effective and helpful while remaining as unobtrusive as possible. The automatic state recording and restoration allow users to maintain flow and continuity within the VR experience enhances overall accessibility and usability.

The recentering prompts are designed to include various feedback mechanisms, ensuring that users are aware of the need to recenter and can respond promptly. Key elements include visual cues, auditory signals, haptic feedback, and continuous transitions. The system provides clear visual indicators within the VR environment to alert users when recentering is required. These cues are designed to be easily noticeable without disruptive the ongoing interaction. In addition to these visual cues, the system can emit auditory signals to notify users of the need to recenter. These sounds are designed to be distinct yet not startling, ensuring users can recognize them without looking directly at the visual cues. For users with compatible devices, haptic feedback can provide a tactile alert. This feedback can benefit users with visual or auditory impairments, ensuring they receive the recentering prompt through another sensory channel. To ensure user comfort, the system uses smooth fade-in and fade-out transitions to maintain user continuity when recentering the viewpoint. This approach avoids a sudden change in viewpoint, which could cause discomfort or disorientation. Instead, the viewpoint adjusts smoothly, allowing the user to maintain their sense of immersion and spatial orientation.

Other features and aspects of the invention will become apparent from the following detailed description, taken in conjunction with the accompanying drawings, which illustrate, by way of example, the features in accordance with embodiments of the invention. The summary is not intended to limit the scope of the invention, which is defined solely by the claims attached hereto.

BRIEF DESCRIPTION OF THE DRAWINGS

The various embodiments are illustrated by way of example, and not by way of limitation, in the figures of the accompanying drawings. Having thus described the invention in general terms, reference will now be made to the accompanying drawings, which are not necessarily drawn to scale, and wherein.

DETAILED DESCRIPTION OF THE PREFERRED EMBODIMENT

Figure 1:
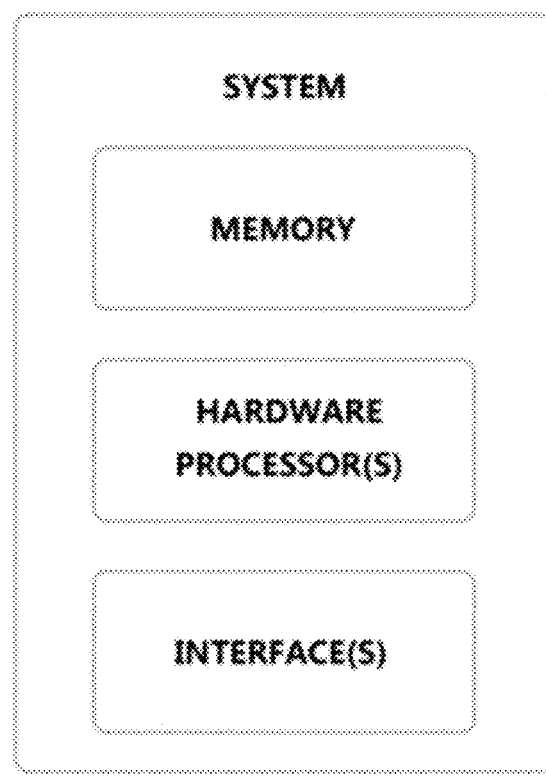
FIG. 1 is a diagram of the VR hardware system.

FIG. 1 is a diagram of the VR hardware system. In accordance with the preferred embodiment of the present invention, the system may include at least one memory, at least one hardware processor, and at least one interface. The platform and system are all components of an exemplary operating environment in which embodiments of the present invention may be implemented. The system may optionally include one or more user computers, computing devices, or processing devices which can be used to operate a client, such as a dedicated application, web browser, etc. The user computers can be general purpose personal computers (including, merely by way of example, personal computers and/or laptop computers running a standard operating system), cell phones or PDAs (running mobile software and being Internet, e-mail, SMS, Blackberry, or other communication protocol enabled), and/or workstation computers running any of a variety of commercially-available UNIX or UNIX-like operating systems (including without limitation, the variety of GNU/Linux operating systems). These user computers may also have any of a variety of applications, including one or more development systems, database client and/or server applications, and Web browser applications. Alternatively, the user computers may be any other electronic device, such as a thin-client computer, Internet-enabled gaming system, and/or personal messaging device, capable of communicating via a network (e.g., the network described below) and/or displaying and navigating Web pages or other types of electronic documents. Although the exemplary system is shown with four user computers, any number of user computers may be supported.

In most embodiments, the system may optionally include some type of network. The network can be any type of network familiar to those skilled in the art that can support data communications using any of a variety of commercially available protocols, including without limitation TCP/IP, SNA, IPX, AppleTalk, and the like. Merely by way of example, the network can be a local area network ("LAN"), such as an Ethernet network, a Token-Ring network and/or the like; a wide-area network; a virtual network, including without limitation a virtual private network ("VPN"); the Internet; an intranet; an extranet; a public switched telephone network ("PSTN"); an infra-red network; a wireless network (e.g., a network operating under any of the IEEE 802.11 suite of protocols, GRPS, GSM, UMTS, EDGE, 2G, 2.5G, 3G, 4G, WiMAX, WiFi, CDMA 2000, WCDMA, the Bluetooth protocol known in the art, and/or any other wireless protocol); and/or any combination of these and/or other networks.

The system may also include one or more server computers which can be general purpose computers, specialized server computers (including, merely by way of example, PC servers, UNIX servers, mid-range servers, mainframe computers rack-mounted servers, etc.), server farms, server clusters, or any other appropriate arrangement and/or combination. One or more of the servers may be dedicated to running applications, such as a business application, a Web server, application server, etc. Such servers may be used to process requests from user computers. The applications can also include any number of applications for controlling access to resources of the servers.

The web server can be running an operating system including any of those discussed above, as well as any commercially-available server operating systems. The Web server can also run any of a variety of server applications and/or mid-tier applications, including HTTP servers, FTP servers, CGI servers, database servers, Java servers, business applications, and the like. The server(s) also may be one or more computers which can be capable of executing programs or scripts in response to the user computers. As one example, a server may execute one or more Web applications. The Web application may be implemented as one or more scripts or programs written in any programming language, such as Java®, C, C#, or C++, and/or any scripting language, such as Perl, Python, or TCL, as well as combinations of any programming/scripting languages. The server(s) may also include database servers, including without limitation those commercially available from Oracle®, Microsoft®, Sybase®, IBM® and the like, which can process requests from database clients running on a user computer.

End users, or users that are viewing and using the network platform, all contribute data to the cloud. A web service platform helps secure that data and maintain the service's functionalities. Only authorized users and entities can authorize or unauthorize content and monitor data stored within the web service. The platform's web services help maintain the operations of elements managed by the storage system.

The system may also optionally include one or more databases. The database(s) may reside in a variety of locations. By way of example, a database 620 may reside on a storage medium local to (and/or resident in) one or more of the computers. Alternatively, it may be remote from any or all of the computers, and/or in communication (e.g., via the network) with one or more of these. In a particular set of embodiments, the database may reside in a storage-area network ("SAN") familiar to those skilled in the art. Similarly, any necessary files for performing the functions attributed to the computers may be stored locally on the respective computer and/or remotely, as appropriate. In one set of embodiments, the database may be a relational database, such as Oracle 10g, that is adapted to store, update, and retrieve data in response to SQL-formatted commands.

Figure 2:
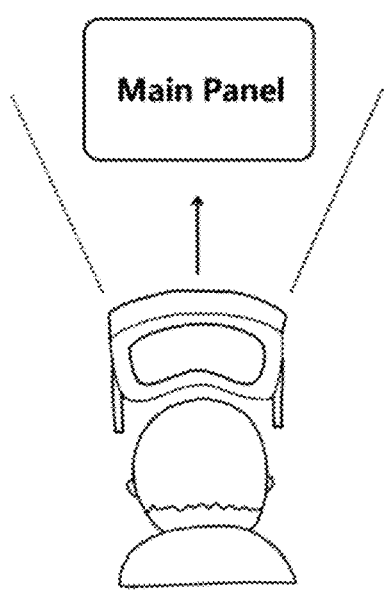
FIG. 2 is a diagram depicting a user looking at a main panel with no or little deviation.

FIG. 2 is a diagram depicting a user looking at a main panel with no or little deviation. In accordance with the preferred embodiment of the present invention, an initialization step determines the initial threshold and waiting time for the system. In an example scenario, a user is engaged in a VR game that requires precise head movements. The initial angular threshold for detecting deviations is set to 20 degrees, with a waiting time of 3 seconds before displaying a recentering prompt. During initialization, the parameters may be:

Initial threshold: $\theta_0 = 200$
Waiting time: $t_r = 3$ seconds
Adjustment Increment: $\Delta\theta = 2°$
History Window N=5 seconds The above may be referred to as the "recentering criterion" which, when exceeded, prompts the system to generate a recentering prompt. The system then continuously monitors the user's viewpoint in relation to the above parameters and adjusts the threshold in real-time, ensuring that the adaptive recentering remains aligned with the user's specific needs and behaviors. The parameters may be customized by the user, providing flexibility to tailor the system's responsiveness according to their specific needs and preferences. Customization options may include and are not limited to angular threshold adjustment, prompt frequency, sensitivity of response, and response time.

Users can modify the initial angular threshold, which determines how much deviation from the central reference point is allowed before a recentering prompt is triggered. This allows users to set a threshold that best suits their comfort level and movement patterns within the VR environment. Users can also adjust how often the system checks deviations and generates recentering prompts. By setting the prompt frequency, users can control how quickly the system responds to significant deviations, ensuring the prompts are timely without being overly intrusive.

The system's responsiveness can be fine-tuned based on user interaction data. Users can customize how the system dynamically adjusts the threshold based on their behavior. For instance, users can set how aggressively the system should increase or decrease the threshold based on their manual adjustments or button presses. Users can also set the waiting time before a recentering prompt is displayed after detecting a deviation. This allows users to balance immediate feedback and giving themselves a chance to self-correct without interruption. By incorporating these adaptive mechanisms and customization options, the system remains responsive to the user's behavior, providing prompts only when necessary and allowing for a more natural and seamless VR experience. This flexibility enhances the overall user experience, making the VR environment more accessible and comfortable for a diverse range of users. Furthermore, the VR device may contain eye-tracking capabilities. In such embodiments, a fixed heads-up display ("HUD") may be implemented in the VR environment which may be configured to follow the user's head movements. Recentering prompts may be generated when the user looks at the HUD for a specified duration, allowing the user to actively recenter by changing their gaze.

Figure 3:
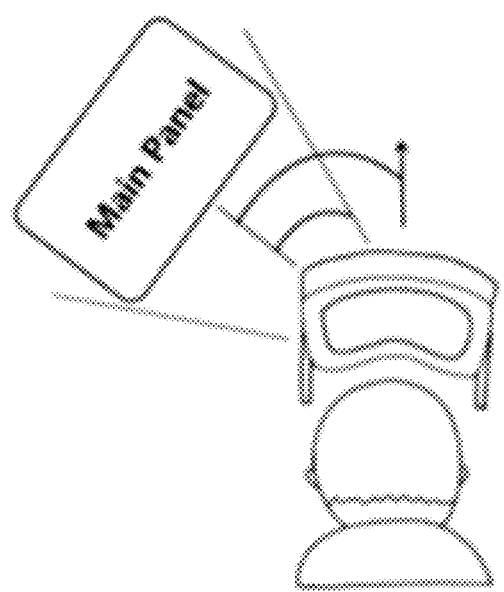
FIG. 3 is a diagram depicting a user's viewpoint deviation angle exceeding a current threshold.

FIG. 3 is a diagram depicting a user's viewpoint deviation angle exceeding a current threshold. In accordance with the preferred embodiment of the present invention, following the initialization, the system continuously monitors the user's head movements using sensors comprising gyroscopes and accelerometers. The current deviation angle $\theta(t)$ is calculated in real time. Suppose the user turns their head, and the system detects a deviation angle of 25°. Since $\theta(t)=25°$ now exceeds the threshold of $\theta_0=20°$, a timer is started. If the deviation persists beyond the predetermined waiting time of $t_t=3$ seconds, the system generates a recentering prompt. The prompt is displayed within the VR environment with visual, auditory, and haptic feedback to alert the user. Prompt visuals may include text, images, shapes, or other graphics. The display of the visual prompt may flash, pulse, fade, move, or remain stationary in the user's field of vision. Auditory prompts may be spoken verbal commands, non-verbal sounds including but not limited to pings, alarms, chimes, or other auditory cues. Haptic feedback may comprise rhythmic or non-rhythmic vibrations, pulses, buzzing, or other modes of haptic feedback. Before displaying the prompt, the system records the player's current state, such as a highlighted option in their interface, to ensure a seamless return to their flow post-recentering. If the user actively responds to the prompt, the system records this as a "successful response." If the user ignores the prompt and manually adjusts their head position within the threshold this is recorded as an "automatic recovery."

To minimize disruption, the prompt is designed to be easily accessible and intuitive. The prompt may contain a menu comprising an option for the user to confirm recentering and an option to dismiss the prompt. The system may automatically highlight the recenter option, enabling users to quickly and effortlessly respond to the prompt. Whether the user responds to the recentering prompt by pressing a button or manually adjusts their view to return within the acceptable range, the system ensures a seamless transition by automatically restoring the previously recorded states after recentering the user's view. For example, this may include resetting a highlighted option to its original state, allowing users to continue their menu interaction without interruption. By implementing these steps, the system ensures that the recentering process is effective and helpful while remaining as unobtrusive as possible. The automatic state recording and restoration allow users to maintain flow and continuity within the VR experience enhances overall accessibility and usability.

The recentering prompts are designed to include various feedback mechanisms, ensuring that users are aware of the need to recenter and can respond promptly. Key elements include visual cues, auditory signals, haptic feedback, and continuous transitions. The system provides clear visual indicators within the VR environment to alert users when recentering is required. These cues are designed to be easily noticeable without disruptive the ongoing interaction. In addition to these visual cues, the system can emit auditory signals to notify users of the need to recenter. These sounds are designed to be distinct yet not startling, ensuring users can recognize them without looking directly at the visual cues. For users with compatible devices, haptic feedback can provide a tactile alert. This feedback can benefit users with visual or auditory impairments, ensuring they receive the recentering prompt through another sensory channel. To ensure user comfort, the system uses smooth fade-in and fade-out transitions to maintain user continuity when recentering the viewpoint. This approach avoids a sudden change in viewpoint, which could cause discomfort or disorientation. Instead, the viewpoint adjusts smoothly, allowing the user to maintain their sense of immersion and spatial orientation.

Figure 4:
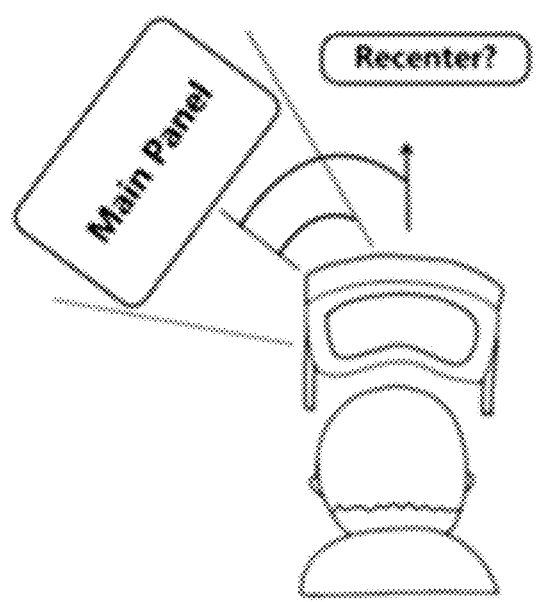
FIG. 4 is a diagram depicting the system generating a recentering prompt due to deviation.

FIG. 4 is a diagram depicting the system generating a recentering prompt due to deviation. In accordance with the preferred embodiment of the present invention, after each event, the system calculates the average deviation angle $\theta_{avg}$ from the recent events. If $\theta_{avg}$ is greater than $\theta_0$ and the user frequently achieves automatic recovery, the threshold is adjusted upwards:

$$\text{New } \theta_0 = \theta_{avg} + \Delta\theta$$

If the user consistently presses the recenter button, indicating the prompt is necessary, and $\theta_{avg}$ is less than $\theta_0$, the threshold is adjusted downwards:

$$\text{New } \theta_0 = \theta_{avg} - \Delta\theta$$

If the user responses are mixed or if there are not enough data points to make a significant change, the threshold may remain the same until more data is collected.

The system continuously monitors the user's viewpoint and makes real-time adjustments to the threshold based on the latest data. This ensures that the adaptive recentering is effective and tailored to the user's specific needs and behaviors. Regardless of whether the user uses the recenter button or manually adjusts their view, the system ensures a smooth transition. The previously recorded state is automatically restored, allowing users to continue their interaction without interruption. The transition involves a smooth fade-in and fade-out to prevent discomfort from sudden angle changes.

Figure 5:
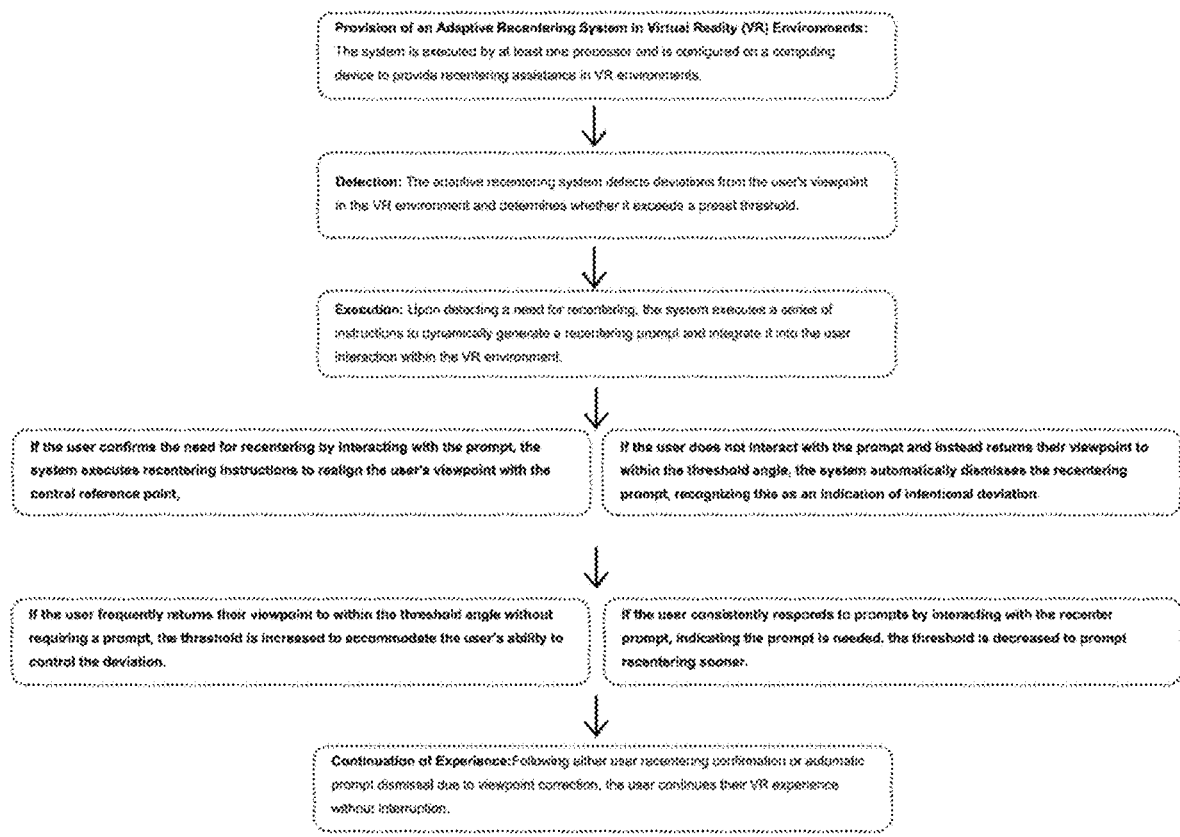
FIG. 5 is a flowchart of the algorithmic steps for detecting viewpoint deviations and generating recentering prompts.

FIG. 5 is a flowchart of the algorithmic steps for detecting viewpoint deviations and generating recentering prompts. In accordance with the preferred embodiment of the present invention, the system is executed by at least one processor and is configured on a computing device to provide recentering assistance in VR environments. Once the system is executed, the adaptive monitoring system detects deviations from the user's viewpoint in the VR environment and determines whether the deviations exceed a preset threshold. Upon detecting a need for recentering, the system executes a series of instructions to dynamically generate a recentering prompt and integrate the prompt into the user interaction within the VR environment.

If the user confirms the need for recentering by interacting with the prompt, the system executes recentering instructions to realign the user's viewpoint with the ventral reference point. If the user does not interact with the prompt and instead returns their viewpoint to within the threshold angle, the system automatically dismisses the recentering prompt, recognizing this as an indication of intentional deviation. If the user frequently returns their viewpoint to within the threshold angle without requiring a prompt, the threshold is increased to accommodate the user's ability to control the deviation. If the user consistently responds to prompts by interacting with the recenter prompt, indicating the prompt is needed, the threshold is decreased to prompt recentering sooner. Following either user recentering confirmation or automatic prompt dismissal due to viewpoint correction, the user continues their VR experience without interruption.

Figure 6:
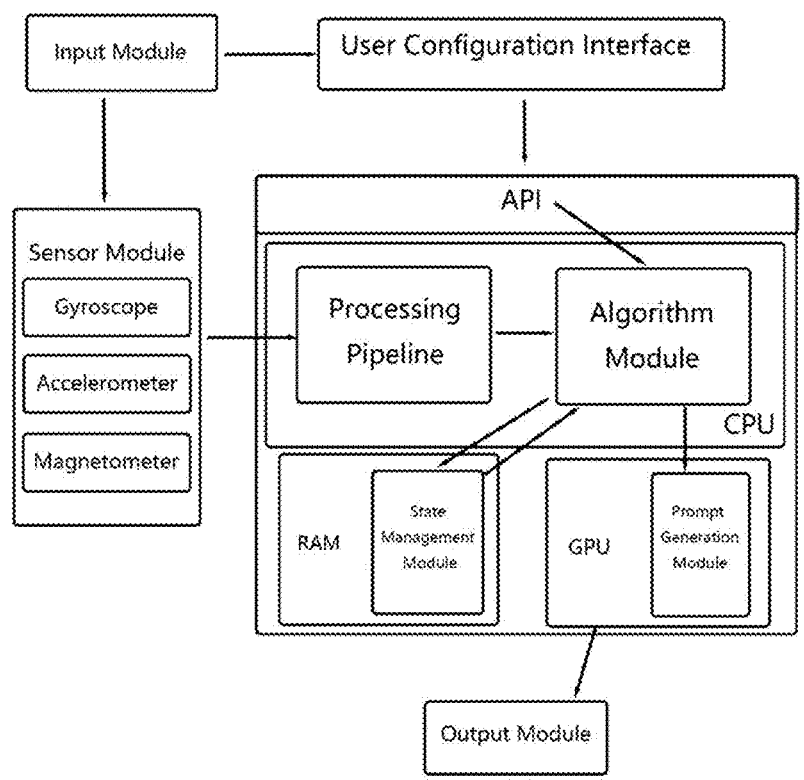
FIG. 6 is a diagram of the system architecture for the adaptive recentering system.

FIG. 6 is a diagram of the system architecture for the adaptive recentering system. In accordance with the preferred embodiment of the present invention, the system may include a sensor module, an input module, and an output module. The sensor module may include a plurality of sensors including at least one gyroscope, at least one accelerometer, at least one magnetometer, and other relevant sensors. In the preferred embodiment, a gyroscope may be configured to determine an angular velocity of the user's head movements, an accelerometer may be configured to determine a linear acceleration and tilt of the user's head, and a magnetometer may be configured to provide an absolute reference point for orientation. In alternative embodiments, the sensor module comprises at least one sensor, wherein said at least one sensor comprises at least one gyroscope, at least one accelerometer, at least one magnetometer, or at least one other relevant sensor. The sensor module may be in communication with an input module and a processing pipeline. The input module is further in communication with a user configuration interface, which in turn is in communication with an application program interface ("API"). The processing pipeline and the API are both in communication with an algorithm module, which is further in communication with the random-access memory ("RAM") which contains the state management module and the graphics processing unit ("GPU") which contains the prompt generation module. The RAM may also contain historical data relating to the user's previous recentering events. The processing pipeline and algorithm module may be contained within the central processing unit ("CPU"). The GPU may be in communication with the output module in order to display the generated prompt to the user. The above may be located on at least one processor, which may be coupled to at least one memory which may be the RAM containing the state management module. The processor may store computer-executable instructions which, when executed, perform the method of the present invention as described herein.

Figure 7:
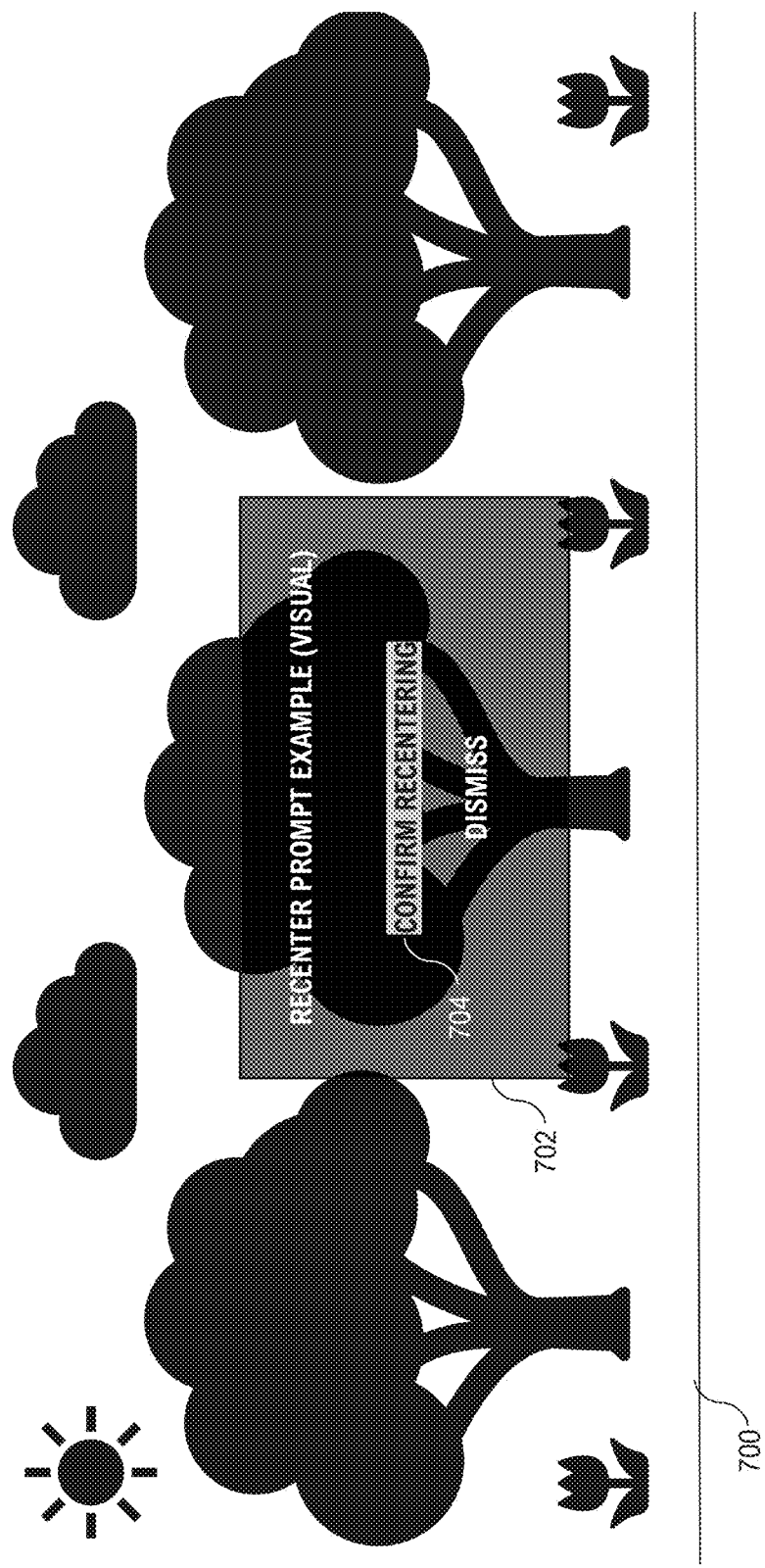
FIG. 7 illustrates an example of the visual recentering prompt.

FIG. 7 illustrates an example of the visual recentering prompt. In accordance with the preferred embodiment of the present invention, a visual prompt may be displayed when a user's viewpoint deviates beyond a designated threshold. Within the user's viewpoint, a prompt 702 may be superimposed onto the view of the VR environment 700. The prompt may include an option to confirm recentering which, if selected, will confirm that the prompt was necessary and will be recorded as a successful response. A user may select the option to confirm the recentering by pressing a designated button, providing a voice command, using gaze-tracking mechanisms, or other means for selecting. The prompt may contain an option to dismiss the prompt which may similarly be selected by various selecting means. The system may automatically highlight the option to confirm the recentering 704 upon displaying the prompt in order to streamline a user's response to the prompt. The prompt may be translucent to ensure minimal disruption to the user's VR experience. In alternative embodiments, the prompt may be opaque or have an adjustable opacity.

Figure 8:
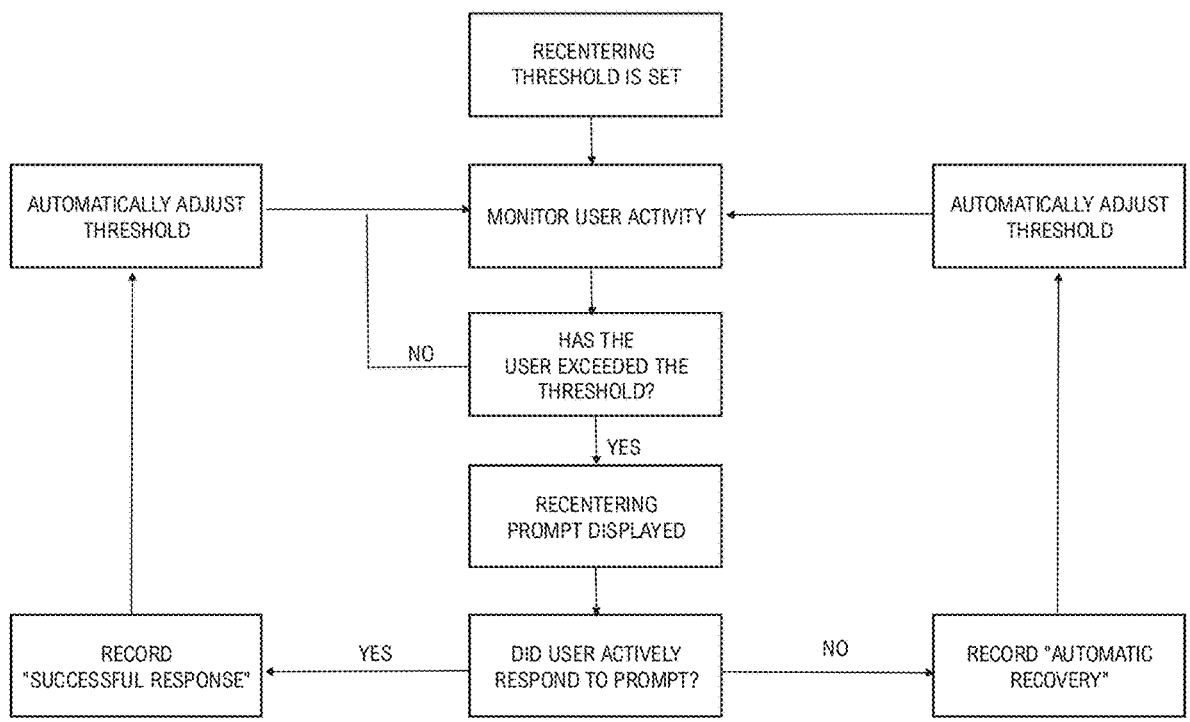
FIG. 8 is a flow chart outlining the method of the present invention.

FIG. 8 is a flow chart outlining the method of the present invention. In accordance with the preferred embodiment of the present invention, a recentering threshold may be set by a user based on the user's preferences. Once the threshold is set, the system begins monitoring the user's activity in the VR environment in order to catch any viewpoint deviations beyond the predetermined threshold. If it is detected that the user has deviated beyond the threshold, a recentering prompt will be displayed. This prompt may be visual, auditory, and/or haptic. The user may actively respond to the prompt or manually correct their viewpoint to be within the designated threshold. If the user actively responds to the prompt, the system will record this as a successful response. If the user manually adjusts their viewpoint, this is recorded as an automatic recovery. This recorded data is analyzed and used to automatically adjust the threshold to better suit the user's viewpoint habits. The automatic adjustments may increase the threshold, decrease the threshold, or affirm the current threshold (i.e. make no change to the current threshold).

Figure 9:
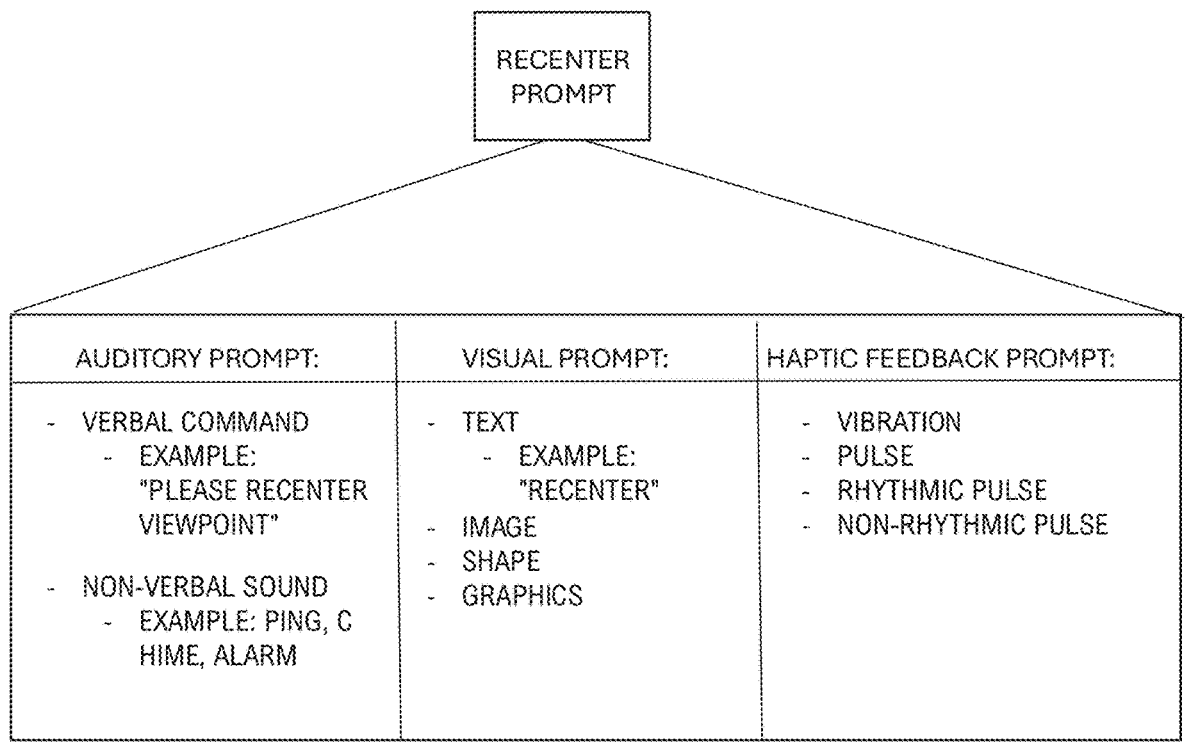
FIG. 9 illustrates the various visual, auditory, and haptic prompts.

FIG. 9 illustrates the various visual, auditory, and haptic prompts. In accordance with the preferred embodiment of the present invention, the recentering prompt may be presented in a plurality of modalities. For example, and not by way of limitation, the prompt may be auditory, visual, or haptic. Auditory prompts may include verbal commands in the user's preferred language, non-verbal sounds including chimes, pings, alarms, or other auditory signals. A visual prompt may include text in the user's preferred language, images, shapes, and other graphics. Haptic prompts may include vibrations, rhythmic pulses, nonrhythmic pulses, or other tactile notifications.

While various embodiments of the disclosed technology have been described above, it should be understood that they have been presented by way of example only, and not of limitation. Likewise, the various diagrams may depict an example architectural or other configuration for the disclosed technology, which is done to aid in understanding the features and functionality that may be included in the disclosed technology. The disclosed technology is not restricted to the illustrated example architectures or configurations, but the desired features may be implemented using a variety of alternative architectures and configurations. Indeed, it will be apparent to one of skill in the art how alternative functional, logical or physical partitioning and configurations may be implemented to implement the desired features of the technology disclosed herein. Also, a multitude of different constituent module names other than those depicted herein may be applied to the various partitions. Additionally, with regard to flow diagrams, operational descriptions and method claims, the order in which the steps are presented herein shall not mandate that various embodiments be implemented to perform the recited functionality in the same order unless the context dictates otherwise.

Although the disclosed technology is described above in terms of various exemplary embodiments and implementations, it should be understood that the various features, aspects and functionality described in one or more of the individual embodiments are not limited in their applicability to the particular embodiment with which they are described, but instead may be applied, alone or in various combinations, to one or more of the other embodiments of the disclosed technology, whether or not such embodiments are described and whether or not such features are presented as being a part of a described embodiment. Thus, the breadth and scope of the technology disclosed herein should not be limited by any of the above-described exemplary embodiments.

Terms and phrases used in this document, and variations thereof, unless otherwise expressly stated, should be construed as open ended as opposed to limiting. As examples of the foregoing: the term "including" should be read as meaning "including, without limitation" or the like; the term "example" is used to provide exemplary instances of the item in discussion, not an exhaustive or limiting list thereof; the terms "a" or "an" should be read as meaning "at least one," "one or more" or the like; and adjectives such as "conventional," "traditional," "normal," "standard," "known" and terms of similar meaning should not be construed as limiting the item described to a given time period or to an item available as of a given time, but instead should be read to encompass conventional, traditional, normal, or standard technologies that may be available or known now or at any time in the future. Likewise, where this document refers to technologies that would be apparent or known to one of ordinary skill in the art, such technologies encompass those apparent or known to the skilled artisan now or at any time in the future.

What is claimed is:

1. A system for adaptive recentering of a user's viewpoint in a virtual reality ("VR") environment of a VR device comprising:
    at least one VR device;
    a plurality of sensors;
    a user configuration interface;
    at least one processor coupled to a memory, wherein said memory stores computer-executable instructions which, when executed, cause said processor to:
        monitor, via said plurality of sensors, real-time head position data of said user;
        detect changes in said real-time head position data in relation to predetermined recentering criterion of head position data;
        generate a recentering prompt when said recentering criterion are exceeded;
        present said recentering prompt to said user;
        record a response from said user to said recentering prompt; and
        adjust said recentering criterion based on said response from said user.

2. The system of claim 1, wherein said plurality of sensors comprises at least one gyroscope.

3. The system of claim 1, wherein said plurality of sensors comprises at least one accelerometer.

4. The system of claim 1, wherein said plurality of sensors comprises at least one magnetometer.

5. The system of claim 1, wherein said recentering criterion comprise an initial angular threshold.

6. The system of claim 1, wherein said recentering criterion comprise a waiting time.

7. A method for adaptive recentering of a user's viewpoint in a virtual reality ("VR") environment of a VR device comprising:
    specifying a recentering criterion indicating a need to recenter said user's viewpoint within said VR environment;
    monitoring, via at least one sensor, said user's activity to detect when said recentering criterion are exceeded;
    automatically generating a recentering prompt within said VR environment each time the recentering criterion are exceeded;
    storing said user's current state upon generating said recentering prompt; and
    dismissing said recentering prompt and restoring said user's stored state, allowing continuation of activity in said VR environment once recentering is complete.

8. The method of claim 7, wherein said prompt interrupts said user's current activity and highlights a recentering option.

9. The method of claim 7, wherein said VR device is a device with eye-tracking capabilities, and wherein a fixed heads-up display ("HUD") is implemented in said VR environment to follow said user's head movements, and wherein said recentering prompt is generated when said user looks at said HUD for a specified duration, and wherein recentering is achieved via changing said user's gaze.

10. The method of claim 7, wherein said recentering prompt includes a visual feedback mechanism.

11. The method of claim 7, wherein said recentering prompt includes an auditory feedback mechanism.

12. The method of claim 7, wherein said recentering prompt includes a haptic feedback mechanism.

13. The method of claim 7, further comprising adjusting a frequency of said recentering prompt based on said user's interaction with previous prompts to enhance user experience.

14. The method of claim 7, wherein said at least one sensor comprises at least one gyroscope, and wherein said at least one gyroscope measures an angular velocity of said user's head movements.

15. The method of claim 7, wherein said at least one sensor comprise at least one accelerometer, and wherein said at least one accelerometer measures a linear acceleration and tilt of said user's head.

16. The method of claim 7, wherein said at least one sensor comprise at least one magnetometer, and wherein said at least one magnetometer provides an absolute reference point for orientation.

17. The method of claim 7, further comprising automatically adjusting an angular threshold based on historical user data and preferences to personalize a recentering experience.

18. The method of claim 17, wherein said angular threshold is dynamically adjusted based on said user's behavior, comprising:
    increasing said threshold when said user achieves automatic recovery without a need for said recentering prompt; and decreasing said threshold when said user responds to said recentering prompt by pressing a recenter button, indicating a necessity for said prompt.

19. A system for adaptive recentering of a user's viewpoint in a virtual reality ("VR") environment of a VR device comprising:
- at least one VR device;
- a plurality of sensors comprising at least one gyroscope, at least one accelerometer, and at least one magnetometer;
- a user configuration interface;
- at least one processor coupled to a memory, wherein said memory stores computer-executable instructions which, when executed, cause said processor to:
  - monitor, via said plurality of sensors, real-time head position data of said user in relation to a plurality of recentering criterion;
  - detect, via said plurality of sensors, an angle deviation exceeding a threshold angle of deviation of said user's viewpoint from a center point;
  - generate a recentering prompt when said recentering criterion are exceeded;
  - display, within said VR device, said recentering prompt to said user;
  - record a response from said user to said recentering prompt;
  - store said response in said memory;
  - analyze, via an algorithm module associated with said processor, historical data stored in said memory and related to at least one past user response to at least one past recentering prompt; and
  - automatically adjust said recentering criterion based on said response from said user.

20. The system of claim 19, wherein said recentering criterion are dynamically adjusted based on said user's behavior, said adjustments comprising:
- increasing said threshold when said user achieves automatic recovery without a need for said recentering prompt; and
- decreasing said threshold when said user responds to said recentering prompt by pressing a recenter button, indicating a necessity for said prompt.

* * * * *